(12) United States Patent
Schässburger et al.

(10) Patent No.: US 10,342,519 B2
(45) Date of Patent: Jul. 9, 2019

(54) TROCAR ARRANGEMENT FOR TISSUE SAMPLING DEVICE

(71) Applicant: NEODYNAMICS AB, Lidingö (SE)

(72) Inventors: Kai-Uwe Schässburger, Lidingö (SE); Michael Svedberg, Halmstad (SE); Michael Sanell, Haverdal (SE); Pontus Gedda, Haverdal (SE); Mattias Gellett, Halmstad (SE); Magnus Olsen, Vallentuna (SE)

(73) Assignee: NEODYNAMICS AB, Lidingo (SE)

( * ) Notice: Subject to any disclaimer, the term of this patent is extended or adjusted under 35 U.S.C. 154(b) by 216 days.

(21) Appl. No.: 15/518,778

(22) PCT Filed: Oct. 2, 2015

(86) PCT No.: PCT/EP2015/072825
§ 371 (c)(1),
(2) Date: Apr. 13, 2017

(87) PCT Pub. No.: WO2016/058845
PCT Pub. Date: Apr. 21, 2016

(65) Prior Publication Data
US 2017/0238913 A1  Aug. 24, 2017

(30) Foreign Application Priority Data
Oct. 13, 2014  (EP) .................................. 14188606

(51) Int. Cl.
*A61B 10/00* (2006.01)
*A61B 10/02* (2006.01)

(52) U.S. Cl.
CPC ...... *A61B 10/0275* (2013.01); *A61B 10/0233* (2013.01); *A61B 10/0283* (2013.01); *A61B 2010/0208* (2013.01)

(58) Field of Classification Search
CPC . A61B 10/02; A61B 10/0208; A61B 10/0233; A61B 10/0266; A61B 10/0283
See application file for complete search history.

(56) References Cited

U.S. PATENT DOCUMENTS

| 4,735,215 A | 4/1988 | Goto et al. |
| 5,121,751 A | 6/1992 | Panalletta |

(Continued)

FOREIGN PATENT DOCUMENTS

| DE | 20211934 U | 10/2002 |
| EP | 0 966 920 | 12/1999 |

(Continued)

OTHER PUBLICATIONS

International Search Report for corresponding International Patent Application No. PCT/EP2015/072825 dated Nov. 3, 2015.

*Primary Examiner* — Christian Jang
(74) *Attorney, Agent, or Firm* — Renner, Otto, Boisselle & Sklar, LLP

(57) ABSTRACT

An arrangement for taking a biopsy in a human or animal tissue, comprising an elongated hollow member, comprising a proximal end and a distal end, wherein the elongated hollow member has a circular cross-section in a plane perpendicular to a longitudinal axis of said hollow member, and said distal end is provided with a cutting edge. The arrangement further comprising an elongated rod configured to fit inside said elongated hollow member, a longitudinal movement generating unit configured to generate an oscillating longitudinal movement of said elongated hollow member, or of an assembly of said elongated hollow member and said elongated rod via a connection assembly. The connection assembly is provided configured to assemble the elongated hollow member and the elongated rod by detachably fixating said elongated rod inside said elongated hollow (Continued)

member in a longitudinal position relative to said elongated hollow member.

12 Claims, 5 Drawing Sheets

(56) References Cited

U.S. PATENT DOCUMENTS

| | | | |
|---|---|---|---|
| 5,188,118 A | 2/1993 | Terwilliger | |
| 5,348,022 A | 9/1994 | Leigh et al. | |
| 5,392,790 A | 2/1995 | Kanner et al. | |
| 5,615,690 A | 4/1997 | Giurtino et al. | |
| 6,086,543 A * | 7/2000 | Anderson | A61B 10/0233 |
| | | | 600/567 |
| 6,120,463 A | 9/2000 | Bauer | |
| 6,702,761 B1 | 3/2004 | Damadian et al. | |
| 7,828,748 B2 | 11/2010 | Hibner | |
| 8,282,573 B2 | 10/2012 | Shabaz et al. | |
| 8,313,444 B2 | 11/2012 | Thompson et al. | |
| 2005/0203439 A1 * | 9/2005 | Heske | A61B 10/0233 |
| | | | 600/566 |
| 2006/0020186 A1 * | 1/2006 | Brister | A61B 5/0002 |
| | | | 600/345 |
| 2007/0032741 A1 | 2/2007 | Hibner et al. | |
| 2007/0032742 A1 * | 2/2007 | Monson | A61B 10/0275 |
| | | | 600/566 |
| 2009/0012423 A1 | 1/2009 | Peters | |
| 2011/0288437 A1 | 11/2011 | Ryan | |
| 2012/0029354 A1 | 2/2012 | Mark et al. | |
| 2016/0081674 A1 * | 3/2016 | Bagwan | A61B 10/0266 |
| | | | 600/566 |

FOREIGN PATENT DOCUMENTS

| | | |
|---|---|---|
| EP | 1 639 947 | 3/2006 |
| EP | 1 832 234 | 9/2007 |
| EP | 2 138 104 | 12/2009 |
| EP | 2 323 563 | 2/2012 |
| RU | 2212848 | 9/2003 |
| WO | 00/10465 | 3/2000 |
| WO | 2008/115526 | 9/2008 |
| WO | 2012/109621 | 8/2012 |
| WO | 2014/007380 | 6/2016 |

* cited by examiner

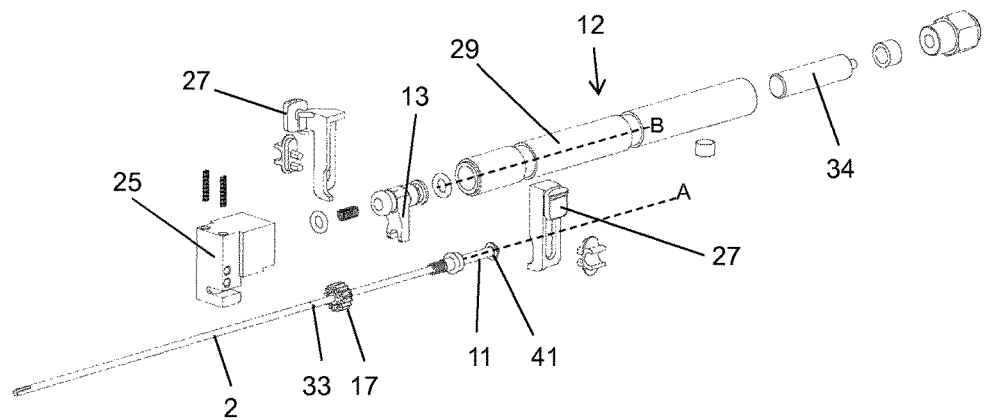
FIG. 5
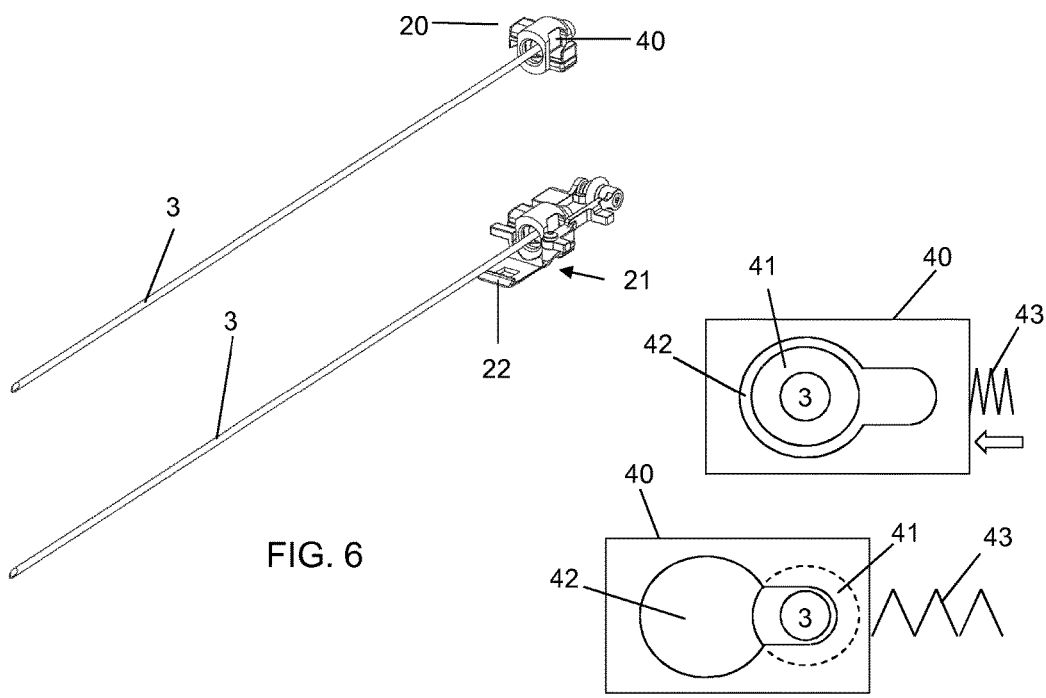
FIG. 6
FIG. 7

TROCAR ARRANGEMENT FOR TISSUE SAMPLING DEVICE

This application is a national phase of International Application No. PCT/EP2015/072825 filed Oct. 2, 2015 and published in the English language, and claims priority to EP 14188606.9 filed Oct. 13, 2014.

FIELD OF THE INVENTION

The present invention relates to an arrangement for invasive procedures in human or animal tissues, in particular to such an arrangement for obtaining a histologic tissue sample, and a method of obtaining a tissue sample during biopsy, according to the preambles of the independent claims.

BACKGROUND OF THE INVENTION

Today it is generally accepted that the final diagnosis of malignancy suspicious lesions has to be confirmed using biopsy techniques. The most commonly performed cell- and tissue-sampling techniques are fine needle aspiration (FNA) using mainly 23 G and 22 G needles (0.6-0.7 mm in diameter) and core needle biopsy (CNB) or vacuum assisted biopsy (VAB) needles using mainly 16-8 G needles (1.6-4.2 mm in diameter), with the latter two techniques dominating globally. Because of the significantly improved sensitivity and minimally invasiveness when combining needle biopsy techniques with imaging guidance the number of open surgical biopsies is steadily declining.

In contrast to FNA, CNB and VAB allow for large volume tissue sampling which permits differentiation between in situ and invasive lesions and histologic diagnosis of microcalcifications.

There are significant advancements when it comes to visualization techniques continuously pushing the boundaries for what is possible when it comes to locating a suspicious lesion. In addition a number of developments like the use of advanced biomarkers for following and personalizing adjuvant treatment are defining new requirements concerning very precise and minimally invasive tissue sampling.

The distal end of biopsy needles used in most CNB and VAB devices is a sharp, solid tip, which is needed for penetration of tissue towards the location where a biopsy is to be taken. To penetrate suspicious lesions the needle has to be inserted manually or using the generally used spring-loaded mechanism to thrust the needle into the lesions with a predetermined length. Thereafter a tissue sampling procedure is initiated, usually incorporating the opening of a residual space which is filled with surrounding tissue and subsequently closed, whereby the tissue inside the residual space is severed from surrounding tissue.

The opening and possible closing of the residual space is usually accomplished by the relative movement of two separate elements of the needle biopsy assembly, e.g. an inner sampling needle relative to an outer cutting needle, an inner trocar relative to an outer sampling needle, or a distal cutting blade relative to a distal tip sampling needle.

Different types of biopsy devices are well known in the art. A few documents describing biopsy devices with hollow needles and elongated rods are US 2012/0029354, U.S. Pat. Nos. 5,188,118, 5,348,022, 5,121,751, 6,120,463, 8,282, 573, 7,828,748, WO 2014/007380, DE 20211934U, U.S. Pat. Nos. 8,313,444, and 5,392,790. In EP 0966920 a fine needle and core biopsy device is disclosed, where the device comprises means for applying rotational and reciprocal movement to a cannula. A core biopsy arrangement has been described by the present applicant in EP2138104 and in EP 2323563, wherein a reciprocating longitudinal movement is applied to a biopsy needle. Further, the following documents describe biopsy arrangements comprising blades or severing arrangements: EP 1832234, WO 0010465, U.S. Pat. No. 5,615,690, RU 2212848, US 2009012423, WO 2008115526.

The sharp, solid tip of biopsy devices used today usually has a length of 5-15 mm. Given that lesions, e.g. in the breast, that can be detected with ultra sound guidance today have a median size of approximately 16 mm and can be as small as 4 mm, a sharp needle tip of such length causes problems. When sampling small tumors the needle tip complicates targeting the lesion. Furthermore the needle tip completely penetrates the lesion, causing unnecessary trauma and risking increased dissemination of tumor cells beyond the original extent of the tumor.

Placing the residual space of the needle inside the lesion is today achieved by either manually or automatically thrusting the needle into the desired location using a spring-loaded or electro mechanic mechanism. The thrust length of automated devices is usually 15-22 mm. CNB and VAB devices do not allow to place the needle precisely even with image guidance due to its significant penetration speed and thrust length. This disadvantage is usually compensated for by increasing the number of tissue sampling procedures or the sample needle diameter, thereby resulting in increased patient discomfort caused by augmented tissue destruction and bleeding. Additionally a fixed thrust length larger than 10 mm is unsuitable for smaller tumors, causing unnecessary patient trauma beyond the dimensions of the lesion.

Additionally, the manual insertion of large diameter needles through healthy tissue towards the targeted lesion can be cumbersome, especially if said tissue is dense. The physician has to apply manual force to navigate the needle towards the lesion while maintaining dexterity and control to not injure vessels and organs. The insertion process is a source of patient anxiety and should therefore be as short and efficient as possible.

To counteract today's shortcomings in biopsy devices a distal tip sampling device is needed that provides samples with a length equivalent to the insertion length into the tumor. Additionally the device should incorporate means to aid insertion through healthy tissue.

Several distinct challenges arise when employing distal-tip tissue arrangements, i.e. where the tissue sample is taken in a longitudinal direction at the distal tip of the biopsy needle.

The first challenge is related to filling the hollow needle with tissue. Preferably, the needle should be filled with tissue equivalent to the insertion length of the needle in the target lesion, i.e. the complete volume should be used for tissue collection to minimize unnecessary patient trauma. This proves problematic, especially taking into account the broad span of tissue properties found in lesions, e.g. in mammary tissue.

The second challenge is related to severing the tissue sample from the surrounding tissue once it is collected inside the hollow sampling needle. It is challenging to apply a reliable cutting mechanism at the distal tip of the needle that works for a broad span of tissue types without significantly increasing the overall cross section of the biopsy needle assembly.

Another challenge relates to the distal tip of the biopsy arrangement. It should be solid during insertion towards the lesion, thus preventing healthy tissue to enter the sampling needle. During insertion into the lesion it should be open and provide a sampling cavity. At the same time the construction must be able to withstand any aid in mechanical energy given to the biopsy arrangement.

Thus an objective of the present invention is to provide a distal-tip biopsy arrangement that reliably and effectively fills the needle with tissue during penetration of the tumor and that can aid insertion of the arrangement towards the lesion through healthy tissue.

SUMMARY OF THE INVENTION

The above-mentioned objective is achieved by the present invention according to the independent claims.

Preferred embodiments are set forth in the dependent claims.

According to a first aspect the invention relates to an arrangement for taking a biopsy in a human or animal tissue, comprising an elongated hollow member, comprising a proximal end and a distal end, wherein the elongated hollow member has a circular cross-section in a plane perpendicular to a longitudinal axis of said hollow member, and said distal end is provided with a cutting edge. The arrangement further comprising an elongated rod configured to fit inside said elongated hollow member, a longitudinal movement generating unit configured to generate an oscillating longitudinal movement of the elongated hollow member, or of an assembly of said elongated hollow member and said elongated rod. A connection assembly is provided configured to assemble the elongated hollow member and the elongated rod by detachably fixating said elongated rod inside said elongated hollow member in a longitudinal position relative to the elongated hollow member. The longitudinal movement generating unit is configured to apply the oscillating longitudinal movement to the elongated hollow member, or of an assembly of the elongated hollow member and the elongated rod via the connection assembly.

According to one embodiment the cutting edge is provided with at least one cutting slit, running from the cutting edge in a proximal direction of the elongated hollow member.

The arrangement further comprises a rotational member configured to apply rotational movement to the hollow member, wherein the rotational movement is applied in accordance to a rotational procedure such that the hollow member is rotated in one direction a predefined amount of rotations, and thereafter rotated in an opposite direction approximately the same predefined amount of rotations. In one embodiment the predefined amount of rotations is a predefined duration of rotation. This results in that the needle rotates in one direction a number of revolutions, and thereafter in an opposite direction approximately the same number of revolutions.

Such an arrangement facilitates filling the needle with tissue using the cutting edge at the distal end of the needle and improves severance of tissue using the rotational movement of the hollow member in cooperation with the cutting slit.

In still a further embodiment, a suction generating unit is configured to apply suction to the sample collection space via a number of small openings in a wall of the hollow member, consequently improving tissue collection by pulling the tissue into the sample collection space by suction, and securing the sample during rotation and retraction.

During the procedure of filling the sample collection space with tissue in particular the features of the distal end cutting edge in combination with applying suction to the sample collection space and by applying the oscillating longitudinal movement to the hollow member, or to the assembly of the hollow member and the elongated rod, have proven to achieve advantageous performance.

During the procedure of cutting the tissue sample in particular the features of providing a cutting slit and applying rotation to the hollow member, and by applying suction to the sample collection space, have proven to achieve advantageous performance.

According to a second aspect, a method for obtaining a biopsy sample using the above mentioned arrangement is also described.

SHORT DESCRIPTION OF THE APPENDED DRAWINGS

FIG. 5 illustrates an exploded view of some of the parts of another arrangement wherein the present invention can be applied.

FIG. 6 illustrates a trocar, connection assembly and sledge of a biopsy arrangement wherein the present invention can be applied.

FIG. 7 is a schematic illustration of the locking member according to one embodiment of the present invention.

DETAILED DESCRIPTION OF PREFERRED EMBODIMENTS OF THE INVENTION

Introduction

The present invention generally relates to an arrangement for invasive procedures in a human or animal tissue, preferably for taking a biopsy.

Throughout the description and figures the same or similar items have the same reference signs.

In order to fully disclose all aspects of the present invention a comprehensive description of the arrangement including features of the present invention and the sampling procedure will be given first. A detailed description of the specific features of the present invention as defined by the independent claims will follow afterwards.

Figure 1:
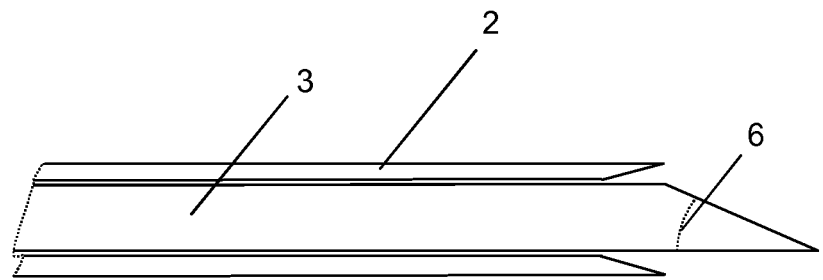
FIG. 1 shows a cross-sectional view of a distal tip of a biopsy needle and trocar during insertion according to the present invention.

A hollow member 2 (a needle) according to the present invention is used together with an elongated rod 3 (a trocar), as illustrated in FIG. 1. A trocar is herein defined as an elongated rod having essentially the same cross-sectional shape as the inner cross-sectional shape of a hollow needle. The outer diameter of the trocar is such that it fits inside the hollow needle and such that it may easily be inserted into and withdrawn from a position within the hollow needle.

Typically, a needle is between 1.2 and 4.2 mm in outer diameter, while the trocar, being adapted to the inner diameter of the needle, can be between 1.0 and 4.1 mm in diameter.

During insertion of the hollow needle 2 into tissue, the trocar 3 is fitted inside the hollow needle. The trocar is in a forward position, i.e. the distal tip of the trocar is located slightly distally, e.g. 0-5 mm, in relation to the distal tip of the hollow needle, as shown in FIG. 1. Thereby tissue is prevented from entering the hollow needle and penetration of tissue towards the target lesion is made possible without filling the hollow needle with healthy tissue. Preferably the trocar 3 is provided with an acutely angled tip, the inclined angle 6 preferably being less than 45 degrees. Naturally other shapes of the distal tip of the trocar are possible, e.g. provided with a centrally positioned distal tip, a double ended bevel grind, trifacet grind, a ball tip grind, a truncated tip grind or a bevel tip grind with secondary angle grind along the outside of the trocar tip. This improves dissection properties for a convenient entry into the tissue regardless of texture.

Mechanical pulses are applied to thrust the biopsy needle assembly, i.e. the hollow needle and trocar in forward position, forward through the tissue. Such movement is preferably performed by alternately moving the hollow member and trocar first forward and thereafter approximately the same distance backwards, i.e. in a reciprocating and oscillating movement along a longitudinal axis. Herein the phrase oscillating longitudinal movement is understood to describe continuous forward and backward movements along a longitudinal axis. This oscillating longitudinal movement of the needle and trocar is performed while the entire arrangement is manually moved forwards into the tissue, towards the target lesion 4 (FIG. 2).

Figure 2:
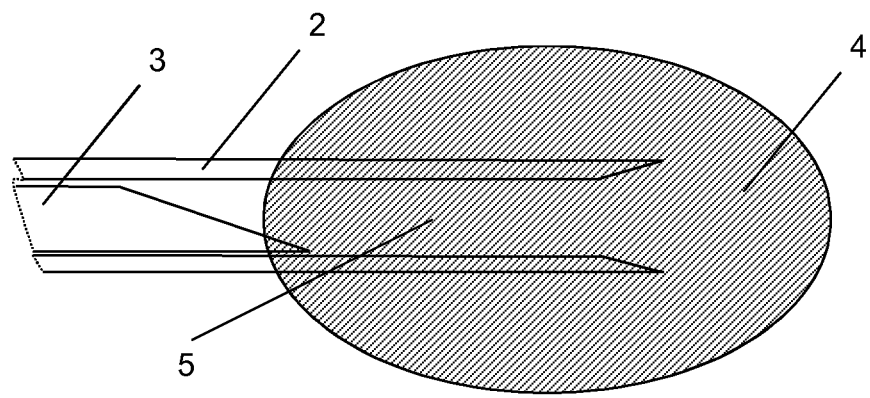
FIG. 2 shows a cross-sectional view of a distal tip of a biopsy needle and trocar during sampling according to the present invention.

FIG. 2 schematically illustrates how a sample may be obtained. When the tip of the assembly is in or adjacent to a sample site or target lesion 4, the trocar 3 is withdrawn a predefined distance, i.e. in the proximal direction, thus creating a residual space 5 for tissue collection inside the hollow needle. The hollow needle 2 is subsequently moved forward into the target lesion 4 to fill the hollow needle 2 with tissue from the target lesion, as shown in FIG. 2. This forward movement is preferably performed with a similar oscillating movement as described above, while manually moving the assembly forward into the lesion. However, in this sampling phase, the oscillating movement only needs to be applied to the hollow member. The trocar has been pulled back and can either be locked in a pulled-back, or retracted, position in relation to the hollow member or, according to a preferred embodiment, be left in a free-floating relationship to the hollow member and thus not oscillate back and forth. During tissue sampling, the distal tip of the trocar 3 is positioned inside the needle 2, e.g. at a distance of approximately 40-80 mm, preferably approximately 60 mm, from the distal end of the hollow needle.

The details of the tissue sampling phase and features of the distal end of the hollow needle will be described below. After tissue sampling is terminated and the needle is withdrawn from the tissue, the sample is removed from the hollow needle 2. During removal of the tissue sample, the trocar 3 is preferably moved in a forward, i.e. distal, direction and used to remove the tissue sample by applying a force in the longitudinal direction towards the distal tip of the needle and thereby pushing out the sample (not illustrated).

The distal end of the trocar is shaped such that it is sharp enough to enable penetration of tissue during the insertion procedure but is also suitable to push out the sample, i.e. not be shaped so that it damages the sample. In an alternative embodiment, tissue removal is performed by manual removal of the tissue sample using e.g. a gripping instrument, such as tweezers, or an aspiration instrument, such as a pipette.

A biopsy arrangement in which the present invention may be applied will now be described. However, the present invention is applicable in any biopsy arrangement wherein a histologic tissue sample is obtained.

Figure 3:
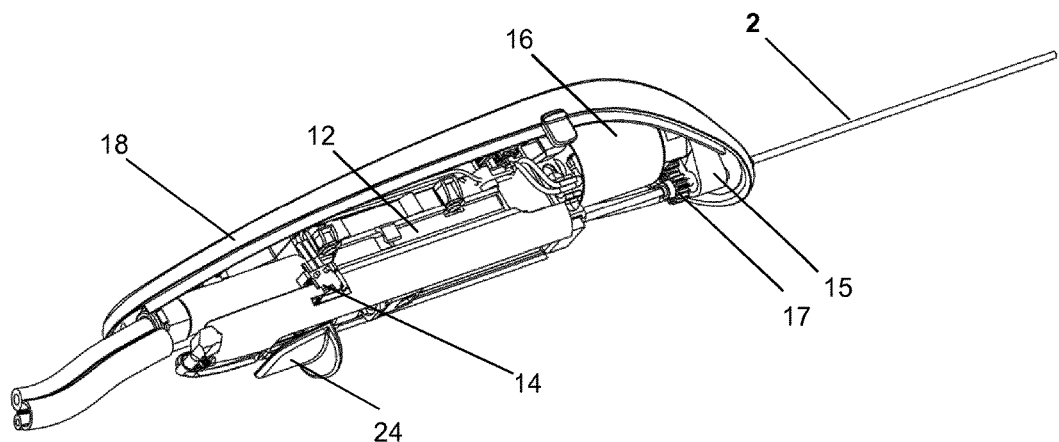
FIG. 3 illustrates a biopsy arrangement wherein the present invention can be applied.
Figure 4:
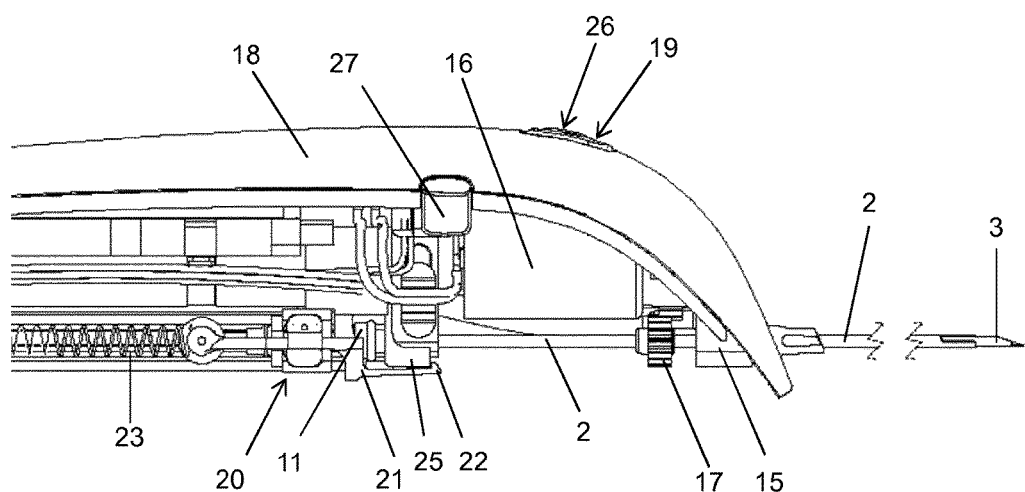
FIG. 4 illustrates a close-up view of a part of the arrangement of FIG. 3.

A biopsy arrangement is shown in FIGS. 3 and 4, wherein a connection assembly 20 is provided which, in accordance with the present invention, is configured to detachably fixate the needle and the trocar to each other. The connection assembly comprises a needle hub 11, and a locking member to lock the trocar 3 to the needle hub 11.

In FIGS. 3 and 4, the arrangement is arranged within a housing 18, enabling the user to grip and easily maneuver the biopsy arrangement. In the figures part of the housing is not shown in order to illustrate features within the housing.

FIG. 5 shows an exploded view of some of the parts of specific details, with housing and electrical cables not shown. Furthermore, some minor details shown in FIG. 5 have no reference sign and are therefore not described.

Description of Movement Generating Unit

As shown in FIG. 5 and in accordance with one embodiment, a longitudinal movement generating unit 12 is configured to generate a longitudinal movement along a longitudinal axis B, such axis being parallel and offset (non-centered) relative to the longitudinal axis A of the combined needle and trocar. The longitudinal movement generated along longitudinal axis B is transferred to longitudinal axis A, and thus to the combined needle and trocar via the connection assembly, as described below.

The longitudinal movement is controlled by an activation button 26 (FIG. 4). By pressing the button down for a short amount of time, only one forward and backward movement of the needle will occur. If the button is held down for a longer time the reciprocating oscillating movement will occur as long as the button is held down. When to apply the oscillating movement on the way towards the tumor depends on the softness of the tissue to be penetrated; in soft tissue it is normally not necessary to activate the longitudinal movement, whereas in more dense tissue the longitudinal movement is very advantageous to use. When penetrating the tumor the oscillating movement is preferably used in order to improve the filling of the needle with tissue.

The longitudinal movement generating unit can be a piston arrangement. Such a piston arrangement comprises a piston 34 arranged to reciprocate in a piston casing 29. This piston arrangement is driven by a movement generating source (not shown), e.g. pressurized air generated by a compressor. In an alternative, the piston arrangement is driven by magnetic forces, hydraulic forces or spring-generated forces. In another alternative, the longitudinal movement generating unit is driven by forces generated by an electric motor or a piezo-electric device. The movement generating source may be located inside the housing or via a connection outside of the housing.

One reason for arranging the movement generating unit 12 with its longitudinal axis B offset with respect to the longitudinal axis A of the combined needle and trocar is related to the presently preferred procedure where the trocar is to be inserted into, and withdrawn from, the needle via the proximal end of the needle. As the longitudinal axes A and B are offset relative to each other, such withdrawal does not require any detachment of e.g. the movement generating unit from the needle and trocar assembly before removing the trocar. If the needle and trocar assembly instead were on the same longitudinal axis, removal of the trocar would be hindered by the presence of the movement generating unit.

However, the distance between longitudinal axis A and longitudinal axis B is preferably as short as possible, e.g. in the range of 0.5-2 cm, such that the leverage from the movement generating unit to the connection assembly required to move the needle can be kept as small as possible.

As illustrated in FIG. 5 and mentioned above, the movement is supplied to the needle arrangement having its longitudinal axis B offset with respect to the longitudinal axis A of the combined needle and trocar. The piston arrangement interacts with the needle via the needle hub 11. Preferably, the piston arrangement interacts with the needle 2 via a piston fork 13 positioned over the needle hub 11, such that longitudinal movement of the piston along axis B is transferred to the needle hub along axis A. However, any other connection to transfer the longitudinal movement from one parallel axis to another can be used.

Notably, the arrangement of using a piston fork 13 to supply the movement enables a rotation of the needle 2.

Furthermore, the needle hub design enables the longitudinal movement of the needle to be faster and longer than the longitudinal movement of the piston fork that transfers the longitudinal movement from the movement generating unit to the needle hub.

Description of Trocar Positioning and Connection Assembly

According to the invention, an elongated rod, a trocar, is arranged inside the hollow member, the needle. During the insertion phase the trocar is positioned in a forward position and fixated to the needle, such that the distal tip of the trocar is close to or slightly in front of the distal tip of the hollow needle, as shown in FIG. 1, effectively hindering any tissue from entering into the hollow needle during the insertion phase. Preferably, the needle and trocar assembly is inserted into tissue using an oscillating longitudinal movement of the fixated needle and trocar in combination with a manual advancement of the entire assembly, as described above, to ensure smooth entry.

After insertion and before the sample collection phase, the trocar is unlocked from the hollow needle and moved back (retracted) in relation to the hollow needle, effectively opening a tissue sampling space within the distal tip of the needle, as shown in FIG. 2. During the sample collection phase, the needle is moved further forward into the desired tissue, preferably using an oscillating longitudinal movement of the needle in combination with a manual advancement of the entire assembly, as described above.

Preferably, the trocar is kept in the pulled back position during retraction of the arrangement, and can be moved forward once the sample is to be released from the arrangement for analysis. The trocar may be used to push the sample out of the hollow needle.

During insertion into tissue, the needle and the trocar are assembled by detachable fixation to each other by the connection assembly 20. Thus, when oscillating longitudinal movement is generated via the connection assembly, the trocar and hollow needle will move in unison, as one unit, into the tissue when moving the arrangement forward towards the lesion.

When a position is achieved such that the distal tip of the needle and trocar is adjacent to or inserted into the desired sample site, the trocar is retracted, such that the trocar can slide independently from the needle. As mentioned above in connection to FIG. 2, the trocar is moved in a proximal direction, and optionally locked in such a proximal position in relation to the needle tip or the housing. Thereafter the needle and/or the entire arrangement is pushed forward, preferably during a simultaneous oscillating longitudinal movement of the hollow needle, allowing tissue to enter the hollow needle through the distal tip opening.

During the sample collection phase, the trocar is pulled back and is preferably not subjected to the oscillating longitudinal movement generated during this phase. Thus, the oscillating longitudinal movement is only applied to the hollow needle during sample collection. Notably, when the trocar is in a free floating position in relation to the needle and the piston generates a fixed amount of energy, the needle movement will be faster compared to the movement of the combined needle/trocar assembly, given the lower weight. This will result in a better filling of the needle with tissue.

The connection assembly 20 comprises a locking member 40 to lock the trocar 3 to the needle hub 11 of the needle 2. The locking member can be in two distinct states. In one state the locking member is closed, thereby locking the needle hub to the locking member. In the other state the locking member is open, enabling to separate the needle hub in distal direction from the locking member. The trocar is extended and retracted via the trocar extension button 24 and trocar retraction button 27 respectively.

FIG. 6 illustrates one embodiment of such a connection assembly 20, and FIG. 7 is a schematic illustration of one embodiment of the locking member 40.

Thus, the trocar 3 is provided with a connection assembly 20 comprising a locking member 40 (see upper image of FIG. 6). The connection assembly is mounted in a sledge 21 (see lower image of FIG. 6), such that the connection assembly 20 can move forward and backwards in relation to the sledge 21. The lower image of FIG. 6 illustrates the trocar including the connection assembly mounted on the sledge.

When the trocar is inserted into the needle and pushed in the distal direction, the needle hub 11 at the proximal end of the needle will lock on to the connection assembly by cooperation with the locking member. When a force in the proximal direction is exerted on the sledge and it is moved backwards, the shape of shackles on said sledge forces the connection assembly 20 to open, thereby making possible a separation of the trocar and needle. This will be explained more in detail below.

When a user wants to prepare the arrangement for insertion into tissue, a trocar extension button 24 (see FIG. 3) is pushed forward until the release catch 22 (FIG. 4) grips the distal end of the piston hat 25, holding the trocar 2 and needle 3 in a joined longitudinal position, wherein the trocar distal tip is positioned essentially at the needle distal tip. Before the release catch 22 grips the proximal end of the piston hat 25, the needle hub 11 will have locked to the connection assembly 20, thereby essentially fixating the trocar 3 to the needle 2.

With references to FIG. 7 the general function of the connection assembly 20 and the locking member 40 will be discussed more in detail. In the illustrated example the locking member is arranged in the connection assembly 20 such that it is movable in a radial direction in relation to the longitudinal axis A of the trocar. In one embodiment the locking member has an essentially rectangular shape and having an even thickness in the range of 3-8 mm. The locking member is provided with a through-going opening 42 having a wider part, to the left in the figure, of a size slightly larger than a proximal enlargement 41 of the needle hub 11 and such that the enlargement may pass through, and a smaller part, to the right in the figure, of a size that is slightly larger than the outer diameter of the main part of the needle hub 11, but smaller than the proximal enlargement 41. The locking member is spring loaded by a spring member 43 in a radial direction in relation to axis A, to the left in the figure, such that the spring urges the locking member in a direction where the needle hub is positioned in the smaller part of the opening 42.

When the connection assembly, and the trocar, is moved distally in relation to the sledge the locking member is forced, e.g. by one or many wedges, to the position where the enlargement 41 may pass through the opening and thereby release the trocar from the needle.

The upper illustration of FIG. 7 shows the locking member in an unlocked state, and the lower illustration shows the locking member in a locked state.

When a position is achieved such that the distal tip of the needle and trocar is adjacent to or inserted into the desired sample site, the trocar is retracted. The release catch 22 is arranged such that a trocar retraction button 27 is adapted to release the catch 22 from the piston hat 25. When the catch 22 is released, the sledge 21 is moved backwards by the force of the spring 23, thereby opening the locking member 40 with the help of the shackles and releasing the trocar 3 from the needle 2. The trocar is thus separated from the needle and is retracted through the force of the spring 23.

Notably, the design of the connection assembly including the locking member and the design of the needle hub enable for a fixation independent of the rotational state of the needle, i.e. it is possible to rotate the needle an arbitrary circumference during sampling and still fixate the trocar to the needle for the subsequent sampling procedure.

Description of Vacuum Unit

In order to apply suction to the needle 2, a suction connector 15 is applied to the needle. The suction connector is connected to a suction source via tubing. Suction is only applied when the trocar is in its retracted position.

As mentioned, suction is applied to the inner space 5 of the hollow needle via a number of small openings 33 in the needle wall (see FIG. 5). These openings are connected via the suction connector 15 to the suction source. Such openings can be arranged anywhere along the hollow needle, but are preferably arranged at a proximal end of the needle, e.g. in the part of the needle arranged within the housing 18, as can be seen in FIG. 3. In the embodiments comprising a trocar 3 arranged within the hollow needle 2, such openings are likewise preferably arranged in a proximal region of the needle, as described, as long as some space is allowed between the inner wall of the needle and the outer surface of the trocar. Thus, the suction flow can be applied via the small openings in the proximal region of the needle wall and further via the space between the inner wall of the needle and the outer surface of the trocar, such that suction is achieved within the tissue sampling space 5 at the distal end of the needle. The suction source may be located inside the housing, or via a connection outside the housing.

Notably, the design of the suction connector 15 enables rotation as well as a longitudinal movement of the needle 2 without deteriorating vacuum inside the needle, which is crucial for filling the needle with tissue and severing it from surrounding healthy tissue.

A position sensing means 14, e.g. a micro-switch, is provided to sense the position of the trocar 3 and can thus determine if the trocar is in an extended or retracted state. If the sensing means senses the trocar to be in retracted position suction is applied to the needle. When the trocar is in an extended position and during penetration of tissue towards the tumour, it is better to avoid suction since healthy tissue and blood could be sucked into the needle.

In a preferred embodiment, suction is applied to the interior space of the hollow needle via the small openings 33 in a wall of the hollow needle, as described above. Such suction can be applied throughout the biopsy procedure, or at least during the sample collection phase and sample separation phase. This ensures a more effective tissue sampling, as the suction will assist by pulling the tissue sample into the sample space of the needle, and also help retain it during separation. Preferably suction is maintained during retraction to ensure that the sample is not lost on withdrawal.

Description of Rotational Unit

The rotation of the needle is achieved by a rotational member 16, such as an electrical motor (see FIGS. 3 and 4). The rotational movement is transferred to the needle via a rotational connector 17. The rotational member 16 may be connected to the needle by a cogwheel, or any other suitable means, such that rotation of the needle in relation to the housing 18 is achieved. A predefined rotational pattern is activated by the rotational button 19.

Notably, the rotational connector must enable the needle to move longitudinally.

During the oscillating longitudinal movement great strain is put on the rotational connector. The configuration of the rotational connector enables it to withstand the mechanical stress of the reciprocating longitudinal movement.

Description of Properties Needed to Achieve Adequate Tissue Filling of the Sampling Needle Longitudinal Movement In the above described biopsy arrangement, the longitudinal movement of the combined needle and trocar, or of the needle, oscillates such that the needle and trocar assembly, or needle only, depending on the procedural stage, repetitively moves forward, i.e. distally, and thereafter backward, i.e. proximally. As mentioned above, in the assembly shown in FIGS. 3-5, this longitudinal movement can be generated by a piston arrangement, preferably driven by pressurised air. Preferably, the forward movement is faster, in some cases several magnitudes faster, than the retracting movement, such as described in EP-2323563, by the present applicant.

The frequency of the oscillating reciprocating movement is between 1-5 Hz, preferably 2-4 Hz. The oscillating movement of at least the hollow needle, together with a manual advancement of the entire biopsy assembly, creates a stepwise advancement of the distal end of the needle.

This enables for a more precise procedure while inserting the needle towards the tumour and into the tumour. As a result there will be less patient trauma, shortened procedure time, less risk for disseminating tumour cells and less risk of bleeding.

The oscillating longitudinal movement of the needle preferably has a velocity of at least 5 m/s in the distal (forward) direction. The final velocity is reached in a time below 50 microseconds. Each forward and backward movement preferably has a stroke length of approximately 1.0-3.0 mm. Such a high velocity over such a short stroke length puts a great strain on the biopsy needle assembly. The configuration of the needle hub facilitates the assembly of the needle and the trocar to withstand the mechanical stress of the reciprocating longitudinal movement.

As mentioned above, the trocar and needle are inserted into tissue with the trocar in a forward position, to prevent tissue from entering the needle, and with the trocar and needle locked together by the locking member. During this insertion phase, the needle and trocar unit are advanced using forward movement of the assembly and the oscillating longitudinal movement described above, by effect of the piston arrangement. When a desired sample site is reached, the trocar is released from the needle hub and slid back to a proximal position, as shown in FIG. 2. Thereafter the needle is advanced into the tissue, again using the oscillating longitudinal movement, to introduce a tissue sample into the hollow needle. Insertion length and thus sample length can be chosen arbitrarily by the physician.

Needle Design

Figure 8:
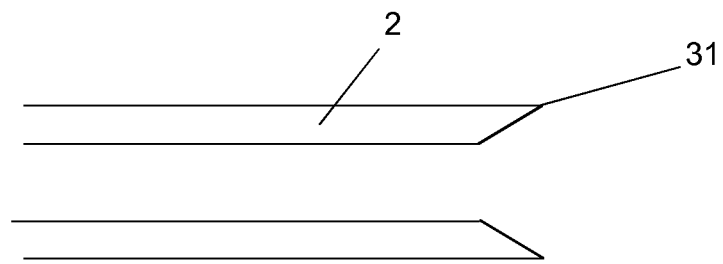
FIG. 8 shows a schematic view of a distal tip of a hollow needle according to prior art.

The distal tip of the hollow needle 2 is preferably provided with an end tip being essentially perpendicular to the longitudinal axis of the needle. In FIG. 8, a preferred embodiment of a distal needle tip is shown. The hollow needle 2 has a distal cutting edge 31 which in one embodiment is a circular cutting edge being essentially perpendicular to the longitudinal axis of the needle 2. Other shapes of the cutting edge are possible, e.g. a saw-tooth shaped along the end tip, a trephine grind on three or more sides, a bevel grind or multi facet grind.

The distal edge 31 is preferably sharpened to enable cutting into the tissue when taking a sample. Such a sharpened edge can be either angled inwards or outwards. In the embodiment shown in FIG. 8, the edge is sharpened inwards, towards the interior of the hollow needle 2, which improves the collection of a tissue sample, as the tissue sample is pushed inwards by the cone-shaped bevelled cutting edge. As an alternative, the edge can be sharpened outwards.

Vacuum/Suction Properties

In one embodiment (which is discussed above), the inner volume of the hollow needle is subjected to a low pressure, i.e. suction, via small openings 33 in the needle wall of the needle (see FIG. 5), which are connected to a suction source via a tubing. Preferably, a suction unit 15 is coupled to the needle 2, as illustrated in FIG. 3. Preferably, suction is applied to achieve approximately 60% or higher vacuum before taking a tissue sample.

In one embodiment the volume to be evacuated is approximately 1 liter. The suction flow in that embodiment can be 10-20 liters per minute at 70% vacuum, preferably approximately 15 liters per minute.

In one preferred embodiment, the inner diameter of the needle is approximately 1.8 mm, and the outer diameter of the trocar is approximately 1.6 mm, thus leaving a space of approximately 0.1 mm radially for suction flow.

Thus, the shape of the distal tip, in combination with the low pressure inside the needle, forces tissue into the interior of the hollow needle, i.e. into the residual space 5 inside the hollow needle, when the needle is moved in a forward direction, preferably with the help of a movement generating unit.

Figure 9:
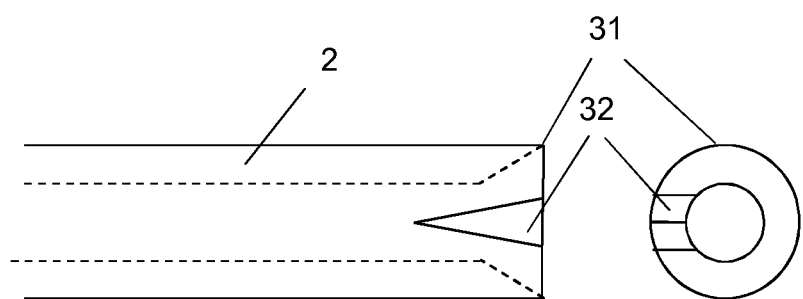
FIG. 9 shows a schematic view of a distal tip of a hollow needle according to one embodiment of the present invention.
Figure 10:
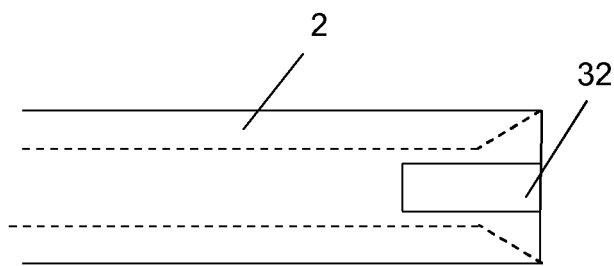
FIG. 10 shows a schematic view of a distal tip of a hollow needle according to another embodiment of the present invention.

Description of Properties Needed to Achieve Adequate Severing of the Tissue in the Sampling Needle from Surrounding Tissue Needle Slit According to one embodiment of the present invention, the distal end of the needle tip is provided with at least one cutting slit in the distal edge of the needle wall. The purpose of providing a slit or several slits is described below. A needle tip including a slit 32 is illustrated in FIG. 9, which shows a side view on the left and a view from the distal end of the needle tip on the right. The slit may be provided with sharpened edges. As an alternative the needle tip can have two or more slits around the circumference of the distal edge. A cutting slit is an essentially V-shaped, U-shaped or square-shaped slit (see FIG. 10) in the needle sleeve, running from the sharp distal edge in the longitudinal direction of the needle. The length of a slit is approximately 1-10 mm and has a width in the cross-sectional plane of the sharp distal edge of approximately 1.0 mm, if the inner diameter of the needle is 1.8 mm.

Rotation

During a biopsy procedure, after filling the needle with tissue, the tissue sample inside the needle must be separated (cut loose) from the surrounding tissue. To achieve this, the needle is subjected to rotation. If the needle is rotated only in one direction, the tissue outside and along the needle may risk sticking to the needle, potentially with the result that the needle is difficult to withdraw and the patient is subject to unnecessary trauma. Therefore, the needle is subjected to rotations in both directions according to a predefined needle rotation procedure. By subjecting the needle to rotations in two different directions of approximately the same amount of rotations, e.g. the same number of revolutions or having the same rotation duration in each direction, the problem of tissue adherence is solved. According to a needle rotation procedure, the needle is first rotated in a first direction at least 1.5 revolutions, and not more than 5-10 revolutions. The rotational speed is approximately 8000-10000 rpm, e.g. approximately 9000 rpm. This first part lasts a first predefined time period, e.g. in the interval 10-40 ms, preferably approximately 30 ms.

After that, the needle is rotated in the other, second direction at least 1.5 revolutions during a second predefined time period. Preferably, this second predefined time period has the same duration as the first predefined time period.

The first and second rotation time periods, i.e. when the needle is rotated in different directions, may be, but are not necessarily, separated by some time period (such as a 30-60 ms pause), during which the rotation member can change polarity, etc.

Thus, the predefined amount of rotations may either be approximately the same predefined rotation duration (e.g. time-based) in each direction, or approximately the same predefined number of revolutions in each direction.

The previously described slit is necessary to cut loose the tissue sample. Without the slit, the sample would rotate inside the needle, especially soft tissue samples that are seldom in a densely packed state. Where the slit is located there is a fixed point in the distal end of the needle at which the sample is fixated, which helps to cut off the sample from the surrounding tissue.

In summary, in accordance with embodiments of the present invention a reliable cutting of the tissue that was inserted into the needle is achieved. The tissue that was forced into the needle is held in the needle compartment by frictional forces of the inner walls of the needle.

In addition, suction is preferably applied to hold the sample within the needle. When cutting loose the tissue sample from the surrounding tissue, an optimal tissue sampling procedure is a result of a combination of the above preferred embodiments, i.e. the distal tip of the needle incorporating a slit, the rotation procedure and applied suction. These features ensure a reliable severance of the collected tissue sample.

Method

Figure 11:
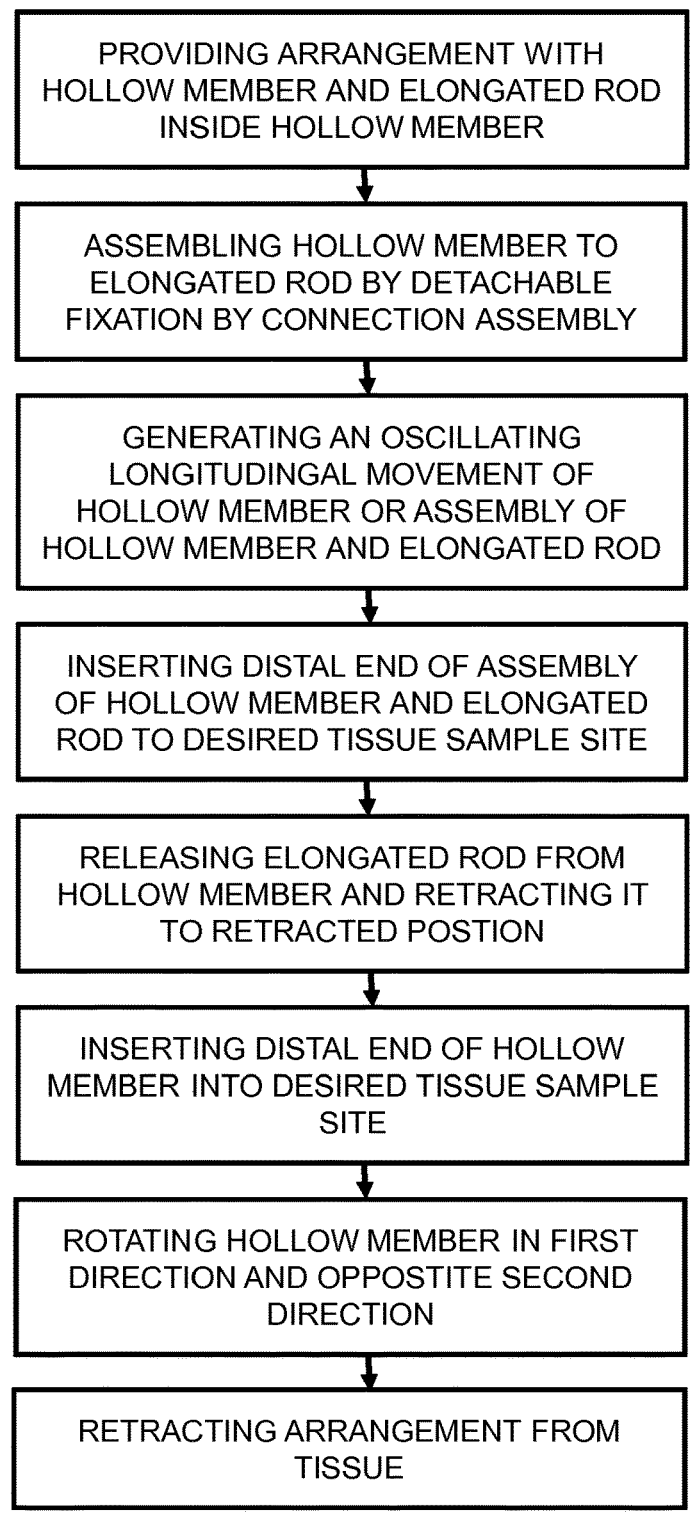
FIG. 11 illustrates a method of using the present invention to obtain a biopsy sample.

In FIG. 11 is shown a flow diagram illustrating a method according to the present invention to obtain a tissue sample during biopsy. The method comprises, providing an elongated hollow member and an elongated rod configured to fit inside the elongated hollow member. And thereafter assembling, by a connection assembly, the elongated hollow member and said elongated rod by detachably fixating the elongated rod inside the elongated hollow member in a longitudinal position relative to the elongated hollow member. The method further comprises generating, by a longitudinal movement generating unit, an oscillating longitudinal movement of the assembly of the elongated hollow member and the elongated rod. And then releasing the elongated rod from the hollow member and retracting the elongated rod to a retracted longitudinal position in relation to said hollow member. The distal end of the elongated hollow member is then inserted into a desired tissue sample site in order to take a tissue sample, preferably by applying a longitudinal movement to the hollow member. The elongated hollow member is rotated in a first direction a predefined amount of rotations, and thereafter rotated in a second opposite direction a second predefined amount of rotations, the first and second predefined amount of rotations being approximately the same, in order to separate the sample tissue from surrounding tissue. Then the arrangement is removed from the tissue site by retraction.

According to one embodiment the method further comprises the step of applying suction to an interior space of the elongated hollow member via small openings in a wall of the elongated hollow member at least during insertion of said distal end of the elongated hollow member into the desired tissue sample site and during rotation of the hollow member. Preferably the suction is applied when the elongated rod is in a retracted position in relation to said hollow member.

The present invention is not limited to the above-described preferred embodiments. Various alternatives, modifications and equivalents may be used. Therefore, the above embodiments should not be taken as limiting the scope of the invention, which is defined by the appending claims.

LIST OF REFERENCE SIGNS

1 Arrangement
2 Elongated hollow member (needle)
3 Elongated rod (trocar)
4 Sample site or target lesion
5 Tissue sampling space
11 Needle hub
12 Longitudinal movement generating unit
13 Piston fork
14 Position sensing means
15 Suction connector
16 Rotational member
17 Rotational connector
18 Housing
19 Rotational button
20 Connection assembly
21 Sledge
22 Release catch
23 Spring
24 Trocar extension button
25 Piston hat
26 Longitudinal movement button
27 Trocar retraction button
29 Piston casing
31 Distal cutting edge
32 Slit
33 Small openings
34 Piston
40 Locking member
41 Proximal enlargement
42 Locking member opening
43 Spring

The invention claimed is:

1. An arrangement for taking a biopsy in a human or animal tissue, comprising an elongated hollow member, comprising a proximal end and a distal end, wherein the elongated hollow member has a circular cross-section in a plane perpendicular to a longitudinal axis of said hollow member, and said distal end is provided with a cutting edge, wherein said arrangement further comprises
an elongated rod configured to fit inside said elongated hollow member,
a longitudinal movement generating unit configured to generate an oscillating longitudinal movement of said elongated hollow member, or of an assembly of said elongated hollow member and said elongated rod, and
a connection assembly configured to assemble said elongated hollow member and said elongated rod by detachably fixating said elongated rod inside said elongated hollow member in a longitudinal position relative to said elongated hollow member, wherein the connection assembly comprises a needle hub attached to said hollow member, and a locking member, configured to be in two distinct states, a locked state and an unlocked state, to respectively lock and unlock the elongated rod to the needle hub, and that said longitudinal movement generating unit is configured to apply said oscillating longitudinal movement to said elongated hollow member, or of the assembly of said elongated hollow member and said elongated rod via said connection assembly.

2. The arrangement according to claim 1, wherein a longitudinal axis B of the longitudinal movement generating unit is offset in relation to a longitudinal axis A of the hollow member or said assembly of said elongated hollow member and elongated rod.

3. The arrangement according to claim 1, wherein said longitudinal position is a forward position where a distal tip of the elongated rod is located slightly distally in relation to the distal tip of the elongated hollow member.

4. The arrangement according to claim 1, wherein said longitudinal movement generating unit is configured to generate an oscillating longitudinal movement where a forward movement is faster than a retracting movement.

5. The arrangement according to claim 1, further comprising a suction generating unit, and a number of small openings in a wall of said elongated hollow member, said suction generating unit being configured to apply suction to an interior space of said elongated hollow member via said openings.

6. The arrangement according to claim 5, wherein said suction is applied when said elongated rod is in a retracted position in relation to said hollow member.

7. The arrangement according to claim 1, wherein said cutting edge is provided with at least one cutting slit, running from said cutting edge in a proximal direction of said elongated hollow member, and that said arrangement further comprises a rotational member, configured to apply rotational movement to said hollow member, wherein said rotational movement is applied in accordance to a rotational procedure such that said hollow member is rotated in one direction a predefined amount of rotations, and thereafter rotated in an opposite direction approximately the same amount of rotations.

8. A method of obtaining a tissue sample during biopsy, the method comprising the steps of:
providing an arrangement comprising an elongated hollow member, having a circular cross-section in a plane perpendicular to a longitudinal axis of said hollow member and comprising a distal end being provided with a cutting edge, providing an elongated rod configured to fit inside said elongated hollow member;

assembling, by a connection assembly, said elongated hollow member and said elongated rod by detachably fixating said elongated rod inside said elongated hollow member in a longitudinal position relative to said elongated hollow member;

generating, by a longitudinal movement generating unit, an oscillating longitudinal movement of the assembly of said elongated hollow member and said elongated rod;

releasing said elongated rod from said hollow member and retracting said elongated rod to a retracted longitudinal position in relation to said hollow member;

inserting said distal end of said elongated hollow member into a desired tissue sample site;

rotating said elongated hollow member in a first direction a predefined amount of rotations;

thereafter rotating said elongated hollow member in a second opposite direction a second predefined amount of rotations, the first and second predefined amount of rotations being approximately the same; and removing said arrangement from the tissue site by retraction.

9. The method according to claim 8, wherein generating an oscillating longitudinal movement includes generating an oscillating longitudinal movement where a forward movement is faster than a retracting movement.

10. The method according to claim 8, further comprising the step of applying suction to an interior space of said elongated hollow member via small openings in a wall of said elongated hollow member at least during insertion of said distal end of said elongated hollow member into said desired tissue sample site and during rotation of said elongated hollow member.

11. The method according to claim 10, further comprising applying said suction when said elongated rod is in a retracted position in relation to said hollow member.

12. The method according to claim 8, wherein releasing comprises unlocking the elongated rod from a needle hub of the connection assembly using a locking member that can be in two distinct states, a locked state and an unlocked state, to respectively lock and unlock the elongated rod to the needle hub.

* * * * *